(12) United States Patent
Pastorello et al.

(10) Patent No.: US 8,901,202 B2
(45) Date of Patent: Dec. 2, 2014

(54) BIOCOMPATIBLE MATERIAL AND PROSTHETIC DEVICE MADE THEREOF FOR THE REPLACEMENT, REPAIR AND REGENERATION OF MENISCUS

(75) Inventors: Andrea Pastorello, Abano Terme (IT); Luigi Ambrosio, Ottaviano (IT); Gennaro Tafuri, Mugnano di Napoli (IT); Alessandra Pavesio, Padua (IT)

(73) Assignees: Luigi Ambrosio, Ottaviano (NA) (IT); Anika Therapeutics S.r.l., Padua (IT)

( * ) Notice: Subject to any disclaimer, the term of this patent is extended or adjusted under 35 U.S.C. 154(b) by 1308 days.

(21) Appl. No.: 11/793,409

(22) PCT Filed: Dec. 14, 2005

(86) PCT No.: PCT/EP2005/056792
§ 371 (c)(1),
(2), (4) Date: Jun. 14, 2007

(87) PCT Pub. No.: WO2006/064025
PCT Pub. Date: Jun. 22, 2006

(65) Prior Publication Data
US 2008/0097605 A1    Apr. 24, 2008

(30) Foreign Application Priority Data
Dec. 15, 2004  (IT) .............. PD2004A0312

(51) Int. Cl.
*A61F 2/00*    (2006.01)
*A61L 24/00*   (2006.01)
(Continued)

(52) U.S. Cl.
CPC ........... *A61F 2/3872* (2013.01); *A61F 2/30965* (2013.01); *A61L 27/26* (2013.01);
(Continued)

(58) Field of Classification Search
USPC ................................. 525/54.3; 523/113, 115
See application file for complete search history.

(56) References Cited

U.S. PATENT DOCUMENTS 5,356,629 A * 10/1994 Sander et al. ................. 424/422
5,520,916 A *  5/1996 Dorigatti et al. ............. 424/402
(Continued)

FOREIGN PATENT DOCUMENTS

EP   1 466 633 A1   10/2004
EP   1 537 883 A2    6/2005
(Continued)

OTHER PUBLICATIONS

Maara et al. Journal of Biomedical Materials Research, 47(3), 1999, 324-335.*

(Continued)

*Primary Examiner* — Liam J Heincer
(74) *Attorney, Agent, or Firm* — Abelman, Frayne & Schwab

(57) ABSTRACT

Herein described is a biocompatible material comprising a polymer matrix based on hyaluronic acid derivatives and poly-εCaprolactone, the process for preparing this material, a prosthetic device constituted by this biocompatible material and a reinforcing material, the process for preparing the prosthetic device, and its use for the partial or total replacement of meniscus, and regeneration of the meniscal fibrocartilage.

27 Claims, 3 Drawing Sheets

(51) Int. Cl.
| | |
|---|---|
| *C08B 37/00* | (2006.01) |
| *C08G 63/48* | (2006.01) |
| *A61F 2/38* | (2006.01) |
| *A61F 2/30* | (2006.01) |
| *A61L 27/26* | (2006.01) |
| *A61L 27/34* | (2006.01) |
| *A61L 27/48* | (2006.01) |
| *A61L 27/56* | (2006.01) |
| *A61F 2/28* | (2006.01) |

(52) U.S. Cl.
CPC ................ *A61L 27/34* (2013.01); *A61L 27/48* (2013.01); *A61L 27/56* (2013.01); *A61F 2/30756* (2013.01); *A61F 2002/2867* (2013.01); *A61F 2002/30062* (2013.01); *A61F 2002/30133* (2013.01); *A61F 2002/30957* (2013.01); *A61F 2002/30971* (2013.01); *A61F 2210/0004* (2013.01); *A61F 2230/0015* (2013.01); *A61F 2310/00365* (2013.01)
USPC ........................... 523/113; 523/115; 525/54.3

(56) References Cited

U.S. PATENT DOCUMENTS

| | | | | |
|---|---|---|---|---|
| 5,939,323 | A * | 8/1999 | Valentini et al. | 435/395 |
| 6,258,122 | B1 * | 7/2001 | Tweden et al. | 623/2.36 |
| 6,294,202 | B1 * | 9/2001 | Burns et al. | 424/488 |
| 6,409,764 | B1 * | 6/2002 | White et al. | 623/16.11 |
| 6,642,213 | B1 | 11/2003 | Pastorello et al. | |
| 6,656,488 | B2 * | 12/2003 | Yi et al. | 424/423 |
| 6,716,251 | B1 * | 4/2004 | Asius et al. | 623/23.58 |
| 7,025,980 | B1 * | 4/2006 | Williams et al. | 424/423 |
| 7,189,392 | B1 * | 3/2007 | Kim et al. | 424/94.1 |
| 7,575,780 | B2 * | 8/2009 | Alexander et al. | 427/226 |
| 2002/0026039 | A1 * | 2/2002 | Bellini et al. | 536/18.7 |
| 2002/0049281 | A1 * | 4/2002 | Zhao et al. | 525/54.3 |
| 2002/0071855 | A1 * | 6/2002 | Sadozai et al. | 424/426 |
| 2003/0021827 | A1 | 1/2003 | Malaviya et al. | |
| 2003/0060448 | A1 * | 3/2003 | Rivarossa et al. | 514/54 |
| 2003/0147935 | A1 | 8/2003 | Binette et al. | |
| 2003/0215483 | A1 * | 11/2003 | Kim et al. | 424/423 |
| 2004/0030408 | A1 * | 2/2004 | Griffin et al. | 623/23.76 |
| 2004/0197311 | A1 | 10/2004 | Brekke et al. | |
| 2005/0037049 | A1 * | 2/2005 | Fusenig et al. | 424/426 |
| 2005/0043813 | A1 | 2/2005 | Kusanagi et al. | |
| 2005/0123505 | A1 * | 6/2005 | Chen et al. | 424/78.27 |
| 2005/0129729 | A1 * | 6/2005 | Schreiner | 424/423 |
| 2005/0244455 | A1 * | 11/2005 | Greenawalt | 424/423 |
| 2006/0040894 | A1 * | 2/2006 | Hunter et al. | 514/54 |
| 2006/0095139 | A1 * | 5/2006 | Ricol et al. | 623/23.72 |
| 2007/0110819 | A1 * | 5/2007 | Pastorello et al. | 424/549 |
| 2008/0220053 | A1 * | 9/2008 | Pastorello et al. | 424/443 |

FOREIGN PATENT DOCUMENTS

| | | | |
|---|---|---|---|
| WO | WO 9961080 A1 | * | 12/1999 |
| WO | WO 0128602 A1 | * | 4/2001 |
| WO | WO 0170293 A1 | * | 9/2001 |

OTHER PUBLICATIONS

Lemarchand, et al., "Polysaccharide-decorated nanoparticles," *European Journal of Pharmaceutics and Biopharmaceutics* 58 (2004)327-341.

Barbault-Foucher, et al., "Design of poly-E-caprolactone nanospheres coated with bioadhesive hyaluronic acid . . . ," *Journal of Controlled Release* 83 (2002) 365-375.

Zamber et al. Articular Cartilage Lesions of the Knee; *Arthroscopy: The Journal of Arthroscopic and Related Surgery;* (1989)5(4):258-268.

Fairbank; Knee joint changes after meniscectomy; *The Journal of Bone and Joint Surgery;* 30B(4) (1948):664-670.

Farng et al. Meniscal repair devices:A clinical and biomechanical literature review; *The Journal of Arthroscopic and Related Surgery;* 20(3) (2004) 273-286.

Peters et al. The current state of meniscal allograft transplantation and replacement; *The Knee* 10 (2003) 19-31.

Sinha et al. Poly-e-caprolactone microspheres and nanospheres: an overview; *International Journal of Pharmaceutics* 278 (2004) 1-23.

Kweon et al.A novel degradable polycaprolactone networks for tissue engineering; *Biomaterials* 24 (2003) 801-808.

Mow et al. Structure and function of articular cartilage and meniscus; *Basic OrthopaedicBiomechanics;* (1991) 143-199.

* cited by examiner

BIOCOMPATIBLE MATERIAL AND PROSTHETIC DEVICE MADE THEREOF FOR THE REPLACEMENT, REPAIR AND REGENERATION OF MENISCUS

FIELD OF THE INVENTION

The present invention relates to the field of prosthetic devices, and in particular to a biocompatible material comprising hyaluronic acid derivatives and poly-εCaprolactone, useful for preparing prosthetic devices together with suitable reinforcing materials, and to the prosthetic device thus obtained, which is able to perform the mechanical and biological functions of the meniscus, and easy to handle and stitch when being surgically implanted. The present prosthetic device can be used for partial or total replacement and/or repair of damaged menisci and/or regeneration of the meniscal fibrocartilage.

BACKGROUND OF THE INVENTION

The meniscus is a fibrocartilage structure in the knee, between the femur and tibia and firmly anchored to the latter. It is more exact to distinguish between the medial or inner meniscus and the lateral or external meniscus. Meniscal fibrocartilage is often inexactly referred to as cartilage, and thought to have the same characteristics and properties as the hyaline cartilage encasing the joints. Actually, meniscal fibrocartilage differs significantly in structure and function from joint cartilage in general and that of the knee in particular, as described by Mow V. C. and co-workers (*Structure and function of articular cartilage and meniscus*. In: Mow V C, Hayes W C, editors. *Basic Orthopedic Biomechanics*. New York; 1991. p. 143-189).

The function of the meniscus is to match the two bones together, absorb shock and distribute weight evenly during the various stages of movement, from walking to running and jumping. Together with the hyaline cartilage, the menisci also reduce friction between the joint heads, while improving joint stability.

Pathologies of the meniscal tissue substantially involve partial or total lesions that may be caused by the knee being twisted abnormally with the foot firmly on the ground or by joint stress in athletes, and they normally lead to the breaking and/or progressive degeneration of the joint cartilage, ending in manifestations of arthrosis (Zamber et al., *Arthroscopy*, 1989; 5:258-268). This is due both to altered load distribution throughout the joint caused by meniscal lesions, and to the fact that vascularisation of the menisci is limited to their periphery (25-30%) and originates from the surrounding soft tissues, i.e. the synovial membrane and capsule. It is from this area alone that the repair processes can originate. Consequently, any damage involving the central part of the menisci is irreparable. Currently, three main methods are being used to treat meniscal lesions: meniscopexy; partial or total meniscectomy; graft.

Meniscopexy can be performed by arthroscopy and is indicated in cases where the meniscus is not broken, but where the vascularised meniscal wall has become dislodged from the joint capsule. The operation consists in stitching the meniscus to the capsule structures, with the formation of a fibrovascular scar that joins the margins of the wound together creating continuity with the adjacent meniscal fibrocartilage. The prognosis in such cases is often good, as the method exploits the capacity for repair of the only vascularised area in the menisci.

Conversely, there are currently no effective methods for treating lesions in the central, non-vascularised part of the meniscus.

In such cases, the alternative is to perform a meniscectomy, again by arthroscopy. This consists in partially or totally excising the meniscus, thus reducing the area of contact and altering the distribution of pressure on the joint. The resulting situation is one of increased strain and areas of persistent high pressure, especially on the tibial plate. This leads to a progressive degeneration of the knee cartilage, which seems to be proportional to the quantity of meniscus that has been removed (Fairbank T J et al., *J Bone Jt Surg [Br]*, 1948, 30:664-670); the basic principle in this type of surgery is therefore to conserve as much of the functional tissue of the meniscus as possible.

When the extent of damage to the meniscus justifies total meniscectomy, the only alternative is to resort to a graft. There are various kinds of meniscus replacements (Farng E et al., *Arthroscopy*, 2004, 20:273-286; Peters G et al., *Knee*, 2003, 10:19-31), however, the traditional approach to recovering physiological function in damaged organs and tissues using replacements made of metal and/or ceramic materials or biological materials has intrinsic limitations, both biological, due to interaction with the organism and/or the possible transmission of pathologies, and mechanical, due to the obvious diversity between the mechanical properties of the replacements and those of the original tissue.

The need is therefore felt for meniscal prosthesis having the required mechanical resistance, but made of biologically compatible materials.

Hyaluronic acid (hereinafter referred to as "HA") is a heteropolysaccharide constituted by D-glucuronic acid and N-acetyl-glucosamine, that is ubiquitous in the organism. HA plays multiple physiological roles, from support for the cells of numerous tissues to joint lubrication and modulation of numerous biological and physiological processes (such as cell proliferation, migration and differentiation), mediated by interaction with its membrane receptor CD44. Moreover, HA is a molecule that, when suitably modified by chemical reaction, gives rise to materials with the biological/physiological characteristics of the starting molecule but which can be processed in various ways, possibly also in association with other natural, semisynthetic or synthetic polymers, as described for example in EP 618 817 B1. The main chemical modifications that can be made to the HA according to the state of the art, are the following:

salification with organic and/or inorganic bases (EP 138 572 B1);

esterification (HYAFF®) with alcohols of the aliphatic, araliphatic, aromatic, cyclic and heterocyclic series (EP 216 453 B1);

inner esterification (ACP®) with a percentage of esterification not exceeding 20%;

amidation (HYADD™) with amines of the aliphatic, araliphatic, cycloaliphatic, aromatic, cyclic and heterocyclic series (EP 1 095 064 B1);

deacetylation on the fraction of N-acetyl-glucosamine (EP 1 312 772 B1);

O-sulphation (EP 702 699 B1);

percarboxylation (HYOXX™) by oxidation of the primary hydroxyl of the N-acetyl-glucosamine fraction (patent application No. EP 1 339 753).

Also known in the art is the possibility of using hyaluronic acid derivatives, possibly in association with natural and/or semisynthetic and/or synthetic polymers, for preparing three-dimensional structures (patent application EP 1 087 797). These structures are shaped as body parts, such as auricular or nasal septum, not intended for bearing load and strain. The process for preparing these structures requires to previously processing the hyaluronic acid derivatives in particular forms such as non-woven fabrics, porous structures or perforated membranes, which are then variously combined together to create the desired final structure. The mechanical properties of the resulting structures are not suitable for bearing loads, and even more to bear the mechanical strain to which the meniscal area is normally exposed. As to the composition of these structures, they are based on hyaluronic acid derivatives, whereas poly-εCaprolactone (PCL) is not mentioned. PCL is a hydrophobic polyester with excellent biocompatibility and low toxicity, the use of which has already been tried and tested in fields such as those of drug delivery (Sinha V R et al., *Int J Pharm*, 2004, 278:1-23) and tissue engineering (Kweon H et al., *Biomaterials*, 2003, 24:801-808). Nevertheless, this polymer has lengthy degradation times and does not have the necessary chemotactic characteristics for the interaction with cells; therefore, a prosthesis mainly constituted by poly-εCaprolactone would hinder the formation of meniscal fibrocartilage, and would be therefore completely unsuitable as meniscal prosthesis.

The need for meniscal prosthetic devices able to actually behave as a stable mechanical support allowing at the same time an effective regeneration of meniscal fibrocartilage, is therefore still felt.

SUMMARY OF THE INVENTION

Now the Applicant found that the association of poly-εCaprolactone with hyaluronic acid derivatives in specific ratios allows obtaining a biocompatible material that is particularly adapted for preparing prosthetic devices comprising the lyophilisate of this material together with strengthening fibres and/or tissues.

These prosthetic devices are completely biocompatible, that is biodegradable, biologically stable, recognised by the cell receptors and metabolised by the cellular route, while at the same time possessing mechanical resistance that enables them to bear load, stretching, traction and friction to which the meniscus is normally exposed, until the physiological fibrocartilage has completely regenerated. Moreover, the present prosthetic devices are prepared by a process that, thanks to the ductility of the present biocompatible material, allows creating within the devices a mesh of intercommunicating pores that can be colonised by cells, both during in vitro culture and after direct in vivo seeding.

Subject of the present invention is therefore a biocompatible material comprising a polymer matrix comprising poly-εCaprolactone and at least a hyaluronic acid derivative, wherein the concentration of poly-εCaprolactone ranges between 20 and 90% by weight with respect to the total weight of the polymer matrix.

Further subject of the present invention is the process for preparing the above said biocompatible material.

Still further subjects of the present invention are the prosthetic devices comprising a reinforcing material in the form of fibres and/or tissues, and a lyophilisate of the above said biocompatible material, optionally coated with hyaluronic acid or a derivative thereof; a process for preparing these devices and their use for the partial or total replacement of meniscus and/or for the regeneration of meniscal fibrocartilage.

Features and advantages of the present invention will be described in detail in the following description.

DETAILED DESCRIPTION OF THE INVENTION

Figure 1:
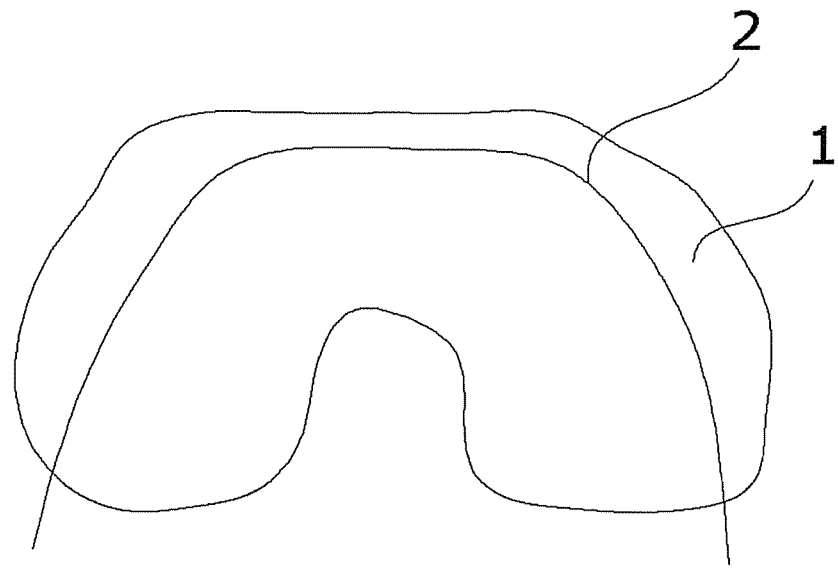
FIG. 1: Model of a prosthetic device for meniscus replacement according to the invention, reinforced with fibres arranged circumferentially inside the matrix.
Figure 2:
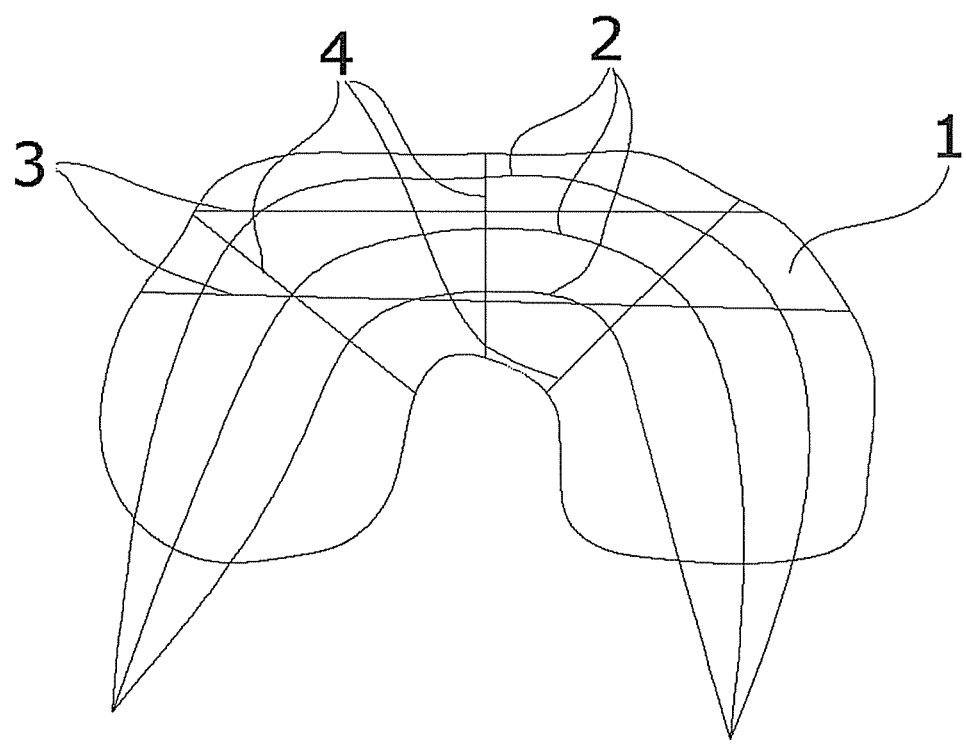
FIG. 2: Model of a prosthetic device for meniscus replacement according to the invention, reinforced with fibres evenly distributed in the matrix.
Figure 3:
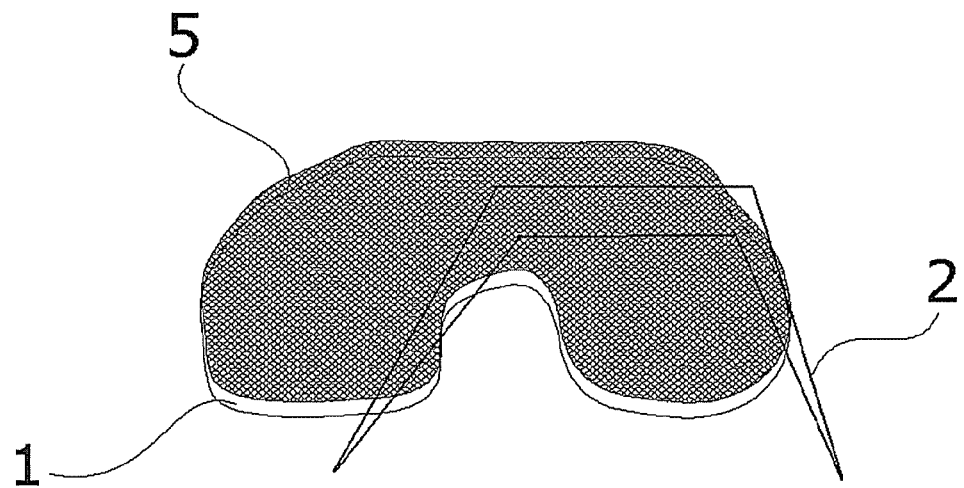
FIG. 3: Model of prosthetic device for meniscus replacement according to the invention, reinforced with a single layer of tissue and with fibres.

The present invention describes a biocompatible material useful for preparing prosthetic devices for the replacement, repair and regeneration of damaged menisci, comprising a polymer matrix comprising poly-εCaprolactone (hereinafter referred to as "PCL") and at least one hyaluronic acid derivative, wherein the percentage of PCL varies between 20 and 90%, preferably between 30 and 70%, and more preferably between 50 and 70% by weight with respect to the total weight of the polymer matrix.

The prosthetic devices according to the invention comprise the lyophilisate of the present biocompatible material and a reinforcing material in the form of tissues and/or fibres, optionally coated by hyaluronic acid or a derivative thereof.

The process for preparing the polymer matrix, described in detail in the following, enables to obtain a matrix having intercommunicating pores where cells can colonise, the proliferation and differentiation of which is favoured by the presence of the hyaluronic acid derivatives. The present prosthetic devices are therefore not only inert mechanical supports but also systems that can induce and favour the repair of damaged meniscal fibrocartilage. At the same time, the polymer matrix has characteristics that enable it to bear the forms of mechanical stress felt at the application site while favouring the formation of new fibrocartilage, reinforced with tissues and/or fibres that mimic the mechanical functions of the collagen fibres of natural meniscus.

The fibres and tissues used as reinforcing material in the present prosthetic device can be constituted by resorbable polymers, such as polylactic acid (PLA), polyglycolic acid (PGA), collagen, and mixtures thereof and/or non-resorbable polymers, such as polypropylene, polyester, polyethylene terephthalate (PET), polytetrafluoroethylene (PTFE), and mixtures thereof.

As regards the present polymer matrix, it is biocompatible, i.e. biologically compatible with the organism in which they are to be implanted, besides being biodegradable and/or biostable, recognisable by the cell receptors and able to be metabolised by the cellular pathway. It is also capable of interacting with the molecules in the extracellular matrix and has suitable chemical-physical characteristics (porosity, hydrophilicity, surface area and surface load) to guarantee cell functions. Lastly, it can be processed for the manufacture of the prosthetic device so as to obtain a device that has the required degradation time, and that can be sterilised and handled easily.

As hyaluronic acid derivatives in the present polymer matrix can be used derivatives selected from the group consisting of:
A) salts of hyaluronic acid with organic and/or inorganic bases,
B) amides of hyaluronic acid with aliphatic, aromatic, arylaliphatic, cycloaliphatic, or heterocyclic amines,
C) esters of hyaluronic acid with aliphatic, aromatic, arylaliphatic, cycloaliphatic, or heterocyclic alcohols,
D) inner esters of hyaluronic acid,
E) deacetylated derivatives of hyaluronic acid,
F) percarboxylated derivatives of hyaluronic acid, and
G) O-sulphated derivatives of hyaluronic acid,
and mixtures thereof.

According to the invention preferred are benzyl esters of hyaluronic acid (HYAFF® 11) having a degree of esterification of from 50 to 100%, and more preferably a degree of esterification of from 75 to 100%.

The preparation process of the present biocompatible material comprises the following steps:
i) preparing a solution of poly-εCaprolactone in a suitable solvent or solvents mixture;
ii) mixing the hyaluronic acid derivative in powder form with a pore-forming agent in an anhydrous environment;
iii) pouring the solution of poly-εCaprolactone coming from step i) onto the mixture coming from step ii) and mixing together, thus obtaining the desired polymer matrix.

Step i) is preferably performed at an initial temperature ranging from 30 to 40° C., using a mixture of tetrahydrofurane, dimethylsulphoxide and ethanol as the solvents mixture. More preferably, the PCL is solubilised with a mixture of solvents consisting of 70.5% by volume of tetrahydrofurane, 19.75% by volume of dimethylsulphoxide and 9.75% by volume of ethanol with respect to the total volume of the solvents mixture.

The pore-forming agent in step ii) may be selected for example from the substances able to generate inert gases, such as carbon dioxide; preferably, the pore-forming agent of the invention is a mixture of citric acid, NaCl and $NaHCO_3$. More preferably, the mixture of salts used as pore-forming agent in step ii) is composed of 93.8% NaCl with granulometry of 315÷400 μm, 3.5% $NaHCO_3$ with granulometry of 140÷400 μm and 2.7% citric acid with granulometry of less than 200 μm.

In the presence of water, a reaction between $NaHCO_3$ and citric acid in the mixture generates carbon dioxide, the purpose of which is to increase the porosity of the NaCl structure and ensure intercommunication between the pores. As a result, the so obtained biocompatible material is able to host the cells that guarantee regeneration of meniscal fibrocartilage.

The weight ratio between PCL and the hyaluronic acid derivative is variable according to the ranges given above, while the weight ratio between the polymers and the mixture of salts is preferably of 1/10.

The mixture described above is made for example in a mechanical mixer, adding first the mixture of salts and the powdered hyaluronic acid derivative about ten minutes later. Lastly, after another 20 minutes, the solution of PCL is added and mixing is continued for about further 40 minutes.

The mixture thus obtained is poured into moulds specially shaped to match the meniscus to be replaced, and used for preparing the present prosthetic devices, comprising a reinforcing material in the form of fibres and/or tissues, and a lyophilisate of the biocompatible material described above.

The process for the preparation of the prosthetic device comprises the following steps:
i') pouring the biocompatible polymer mixture of PCL and hyaluronic acid derivatives into a meniscus-shaped mould;
ii') inserting a reinforcing material in the form of fibres and/or tissues into the polymer mixture;
iii') drying the material coming from step ii') at room temperature, then removing the solidified material from the mould, dipping it into water and carry out one or more washings;
iv') dipping the desiccated and washed material coming from step iii') into water at a temperature of 40° C.;
v') removing water from the material coming from step iv') by lyophilisation by freeze drying technique;
vi') sterilising the so obtained material, for example by irradiation with gamma-rays or by treatment with ethylene oxide.

According to a preferred embodiment of the present process for preparing the prosthetic device, the material coming from freeze-drying in step v') is immersed into an aqueous solution of hyaluronic acid or a derivative thereof, and subjected to one or more cycles of depressurisation and release to room pressure; then water is removed by a second lyophilisation step by freeze drying technique, and the freeze-dried material is finally sterilised.

The reinforcing material used for preparing the present prosthetic device may consist of a bioresorbable polymer, such as polylactic acid (PLA), polyglycolic acid (PGA), collagen and mixtures thereof, and/or of a non-bioresorbable polymer, such as polypropylene, polyester, polyethylene terephthalate, polytetrafluoroethylene and mixtures thereof.

Preferably, in the present prosthetic devices the reinforcing material in the form of fibres consists of polylactic acid, whereas the reinforcing material in the form of tissues consists of polylactic acid and polyglycolic acid.

Figure 4:
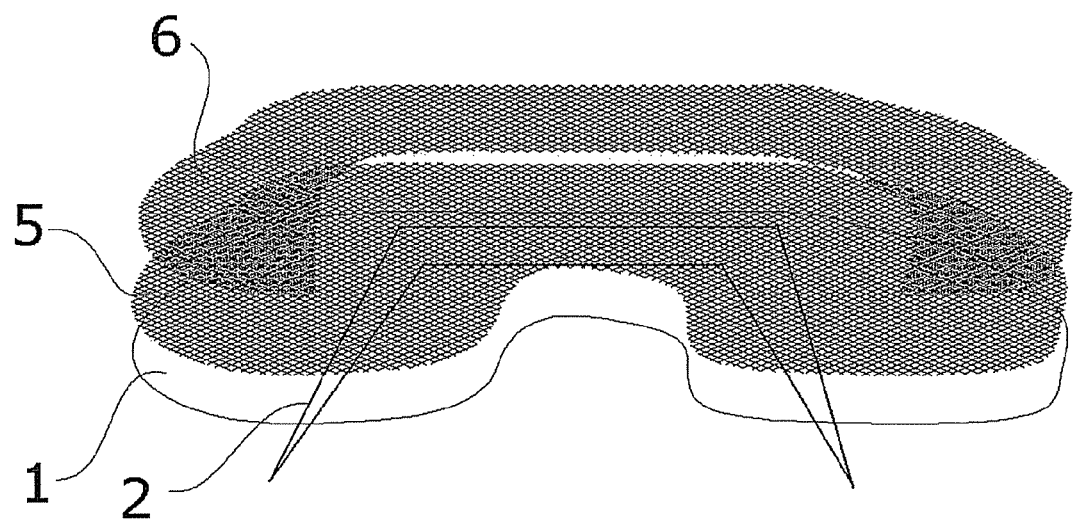
FIG. 4: Model of a prosthetic device for meniscus replacement according to the invention, reinforced with two layers of tissue, one of which is limited to the periphery, and with fibres.
Figure 5A:
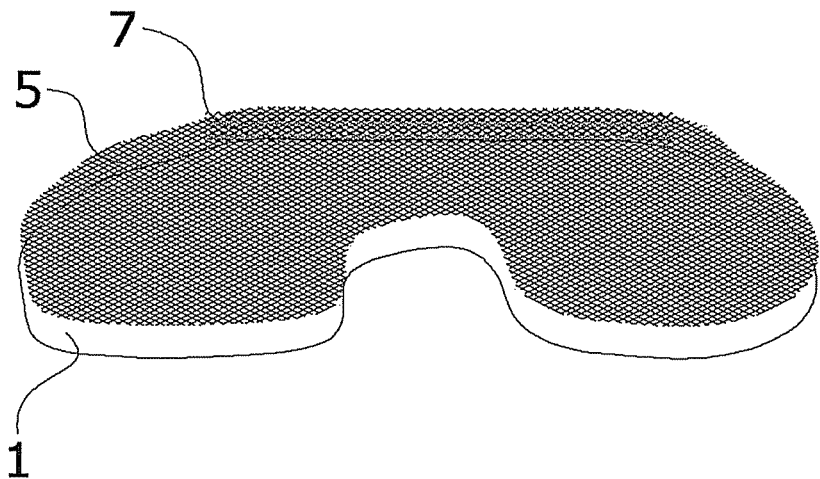
FIG. 5: Model of a prosthetic device for meniscus replacement according to the invention, reinforced with a layer of tissue: a) seen from above, b) frontal view and c) seen from below, and with fibres.
Figure 5B:
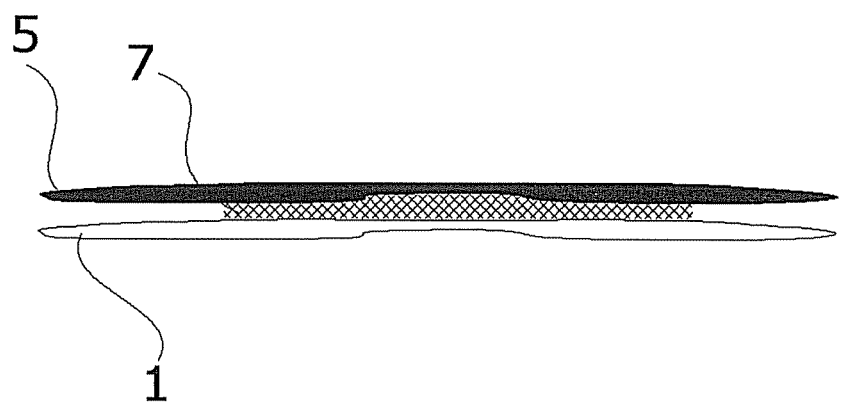
Figure 5C:
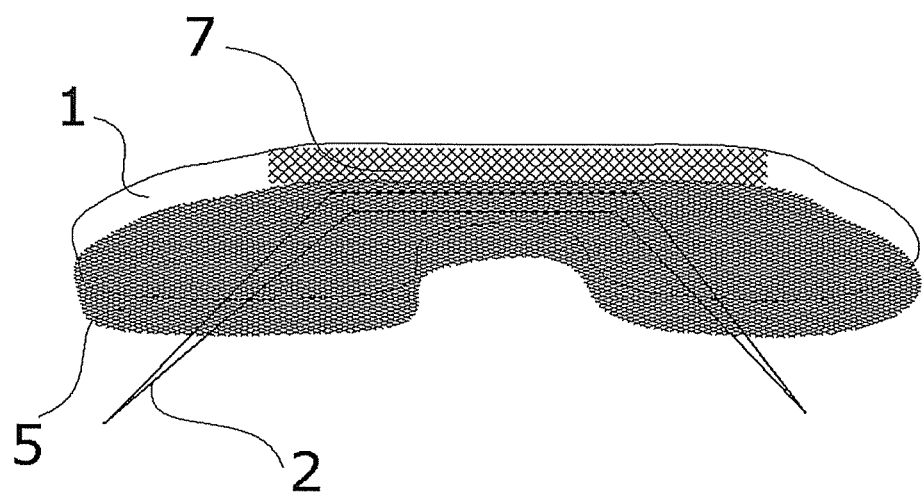

The final prosthetic device may differ on account of the type and position of the reinforcing material included in the polymer mixture during the process; hereinafter are reported some examples of how the steps i') and ii') are carried out according to the invention, and the corresponding devices are illustrated in FIGS. 1-5:
a) the polymer mixture is poured into the mould, up to about ⅔ of its depth. Bioresorbable polymer fibres are then placed circumferentially on top and then another layer of the mixture is added up to the top of the mould; in FIG. 1, the polymer mixture (1) and the fibres (2) are showed;
b) the mould is filled up to ⅔ of its depth with the polymer mixture, then creating the reinforcement by placing bioresorbable polymer fibres circumferentially, horizontally and vertically, then distributing them evenly throughout the matrix, and ensuring that they protrude from the horns so that it is easier to fix the prosthesis to the tibial plate during surgery. The mould is then filled with the remaining mixture; in FIG. 2 the polymer mixture (1), and the fibres in circumferential (2), horizontal (3) and vertical (4) position of the so-obtained device are showed.
c) model reinforced with non-bioresorbable or bioresorbable polymer tissue. In this case, after filling the mould with the polymer mixture up to about ⅔ of its depth and arranging the fibres as in case b), the meniscus-shaped tissue is then placed on top, and lastly the remaining mixture is added. Also in this case the fibres that protrude are useful when fixing the prosthesis to the tibial plate; in FIG. 3 the polymer mixture (1), the fibres (2) and the tissue (5) of the so-obtained device are showed.
d) this prosthetic device is made by forming in the mould the following layers:

a first layer of the polymer mixture;
fibres are placed circumferentially and made to protrude from the horns to facilitate surgical fixture of the prosthesis;
tissue limited to the peripheral area;
further layer of polymer mixture;
complete tissue
and lastly, enough mixture to fill the mould;
in FIG. 4 the polymer mixture (1), the fibres (2), the tissue placed in between the two layers of polymer mixture (5), and the tissue placed in the peripheral area (6) are showed;

e) this prosthetic device is made by first placing tissue around the edge of the mould, then adding the mixture till the mould is ⅔ full, then fibres placed circumferentially as in case b), a second layer of tissue, and then more mixture until the mould is full. A type of reinforcement has also been created where the tissue around the edges is connected with the rest. In FIG. 5 the so obtained device is showed, from above (FIG. 5a), as frontal view (FIG. 5b) and from below (FIG. 5c); besides the polymer mixture (1), the fibres (2), and the tissue (5) placed in between the two layers of polymer mixture, the tissue placed around the edge of the mould (7) is showed.

By varying the distribution and type of the reinforcing material, it is possible to adjust the mechanical properties of the present prosthetic devices, as well as by varying the composition of the polymer matrix, the hydrophilicity of the biocompatible material may be regulated.

Once made as described above, the reinforced material is dried at room temperature, typically for 12 hours, then the material is removed from the mould and immersed in water to remove the solvents and salts, typically for about 12 hours and carrying out more washings with water. Once washed, the material is heat-treated by immersion in water at 40° C., typically for about 5 hours, and then let to cool in the same water. The material is left in water, typically for further 4 days, with daily water changes. Lastly, the devices are lyophilised, preferably by freeze-drying, to remove any water.

According to a preferred embodiment of the invention, after the lyophilisation operation, the devices are coated with hyaluronic acid or a derivative thereof, in order to favour hydration of the biomaterial, promote cellular adhesion and reduce friction between the prosthetic device and the parts of the joint in which it is to be grafted. To achieve this coating, the devices coming from freeze-drying, are immersed in an aqueous solution of hyaluronic acid or a derivative thereof, preferably selected from sodium hyaluronate, inner esters or amides of hyaluronic acid with aliphatic, aromatic, arylaliphatic, cycloaliphatic, or heterocyclic amines; for example an aqueous solution of the sodium hyaluronate at a concentration of 8 mg/ml may be used, with cycles of vacuum and recovery in atmospheric pressure. On completion of this step, the device is lyophilised again, preferably by freeze-drying, to remove any water and further increase the intercommunication between the pores. Lastly, the device is sterilised.

The processes of the invention for preparing the biocompatible material and the prosthetic device, combine wet and/or dry extrusion methods with the addition of pore-forming agents and substances that generate inert gases, such as carbon dioxide; it is also possible to use techniques involving for example supercritical gases to achieve elimination of solvents and reagents from the structures. Other techniques of possible use such as three-dimensional microinjection, bioplotter and 3D printing, well known to any expert in the field, are also within the scope of the present invention.

The prostheses obtained as described above can be loaded with cells, such as:

mesenchymal cells, possibly made to proliferate and/or differentiate in vitro towards the fibrocartilage line by adding suitable growth factors,
cells taken from hyaline cartilage and/or meniscal fibrocartilage, previously grown in vitro,
bone marrow taken from the patient and seeded in the prosthesis directly during surgical application, according to techniques known to any skilled person.

The efficacy and functionality of the present prosthetic devices have also been demonstrated by in vivo studies, when the menisci prosthetic devices according to the present invention were grafted into sheep which had previously undergone partial or total meniscectomy. The grafts successfully supported the joint and favoured regeneration of meniscal cartilage, promoting the formation of new tissue.

For purely descriptive and not limitative purposes, we report hereafter some examples for the preparation of the meniscus replacements that are the subject of the present invention.

EXAMPLE 1

Preparation of a Prosthesis in the Form of a Meniscus Base on HYAFF® 11-p75 and PCL in a Ratio of 30:70, Containing Tissue of PLA/PGA Preparation of the prostheses is performed by a series of steps, namely:
Solubilisation of the poly-εCaprolactone
22.37 g of poly-εCaprolactone (PM 60,000) are dissolved in a mixture of solvents composed of 53.6 ml of THF (tetrahydrofurane), 15 ml of DMSO (dimethylsulphoxide) and 7.4 ml of ethanol (EtOH), at a temperature of 30° C.; a solution of PCL with a concentration of 294 mg/ml is thus obtained.
Preparation of the Mixture of Salts
The following salts are mixed
234.75 g of NaCl crystals with granulometry between 315 and 400 μm
8.75 g of NaHCO$_3$ with granulometry between 140 and 400 μm
6.5 g of citric acid with granulometry lower than 200 μm;
Preparation of the Mixture
To the mixture of salts 9.635 g of HYAFF® 11-p75 are added, and the mixture is then amalgamated for at least 20 minutes in a mechanical mixer. The solution of poly-εCaprolactone is then added and mixing is continued for at least 1 hour.
Filling the Mould
The mould is made with the base of the meniscus facing outwards. Each mould is filled to about 80% of its depth. At this point, a tissue (mesh) of PLA/PGA in a half-moon shape is placed in the mould over the mixture, covering it completely. Further mixture is added until the mould is full.
Coagulation and Washing
The resulting form is left in the mould to dry at room temperature for at least 8 hours, after which it will have solidified in the shape of a meniscus and can be removed from the mould. It is then placed in a bath containing 5 litres of water at room temperature and shaken. The water is changed every four hours and the forms are washed in this way in water for at least 20 hours.
Heat Treatment
The meniscus replacements are placed in a bath containing 3 litres of water which is heated to 40° C. for 5 hours; then left to cool to room temperature.

Lyophilisation by Freeze-Drying

The forms are placed on stainless steel trays for the following freeze-drying cycle:
cooling to a temperature of between −2 and 5° C.
freezing to a temperature of below −30° C.
depressurisation of the freeze-drying chamber to below $10^{(-1)}$ millibar.
heating the trays to a temperature of between −25° C. and −10° C., sublimation for at least 12 hours.
Subsequent heating of the freeze-drying trays to a temperature of between −10° C. and +25° C. for at least 8 hours.

Coating with a Hyaluronic Acid Solution 18 g of hyaluronic acid are dissolved in 2 litres of water and the solution is decanted into a depressurisable container, and the dried forms are added. The container is then sealed and exposed to cycles of depressurisation and release to ambient pressure.

Each cycle involves the container being depressurised to a pressure of below 500 millibar and these conditions being maintained for at least 2 minutes after which ambient pressure is restored. At least 15 cycles of this kind are performed. Freeze-drying is then repeated.

EXAMPLE 2

Preparation of a Prosthesis in the Form of a Meniscus Based on Total HYAFF® 11 and PCL in a Ratio of 40:60, Containing Evenly Distributed PLA Fibres Preparation of the prostheses is characterised by a series of steps, namely:
Solubilisation of poly-εCaprolactone 19.2 g of poly-εCaprolactone (PM 60,000) are dissolved in a mixture of solvents constituted by 46.4 ml of THF (tetrahydrofurane), 13 ml of DMSO (dimethylsulphoxide) and 6.6 ml of ethanol (EtOH), at a temperature of 30° C.

Preparation of the Mixture of Salts

The following salts are mixed
201.24 g of NaCl crystals with granulometry between 315 and 400 μm
7.52 g of sodium bicarbonate with granulometry between 140 and 400 μm
5.59 g of citric acid with granulometry of less than 200 μm;

Preparation of the Mixture

To the mixture of salts 12.8 g of total HYAFF®-11 are added, followed by 20 minutes in a mechanical mixer. The poly-εCaprolactone mixture is then added and amalgamated for at least 30 minutes. Lastly, 1.7 g of PLA fibres (polylactic acid) fibres measuring between 2 and 3 cm long and between 15 and 25 μm in diameter and this is amalgamated for at least 30 minutes.

Once the moulds have been filled and the mixture left to cool to ambient temperature for about 8 hours, the steps of coagulation, freeze-drying, coating and sterilisation can be performed as described in Example 1.

The invention claimed is:

1. A biocompatible material comprising a polymer matrix having intercommunicating pores and consisting of poly-εCaprolactone mixed with a hyaluronic acid derivative, wherein the concentration of poly-εCaprolactone ranges between 30 and 70% by weight with respect to the total weight of the polymer matrix, and wherein said hyaluronic acid derivative is benzyl ester of hyaluronic acid having a degree of esterification of from 50 to 100%.

2. The biocompatible material according to claim 1, wherein the concentration of poly-εCaprolactone ranges between 50 and 70% by weight with respect to the total weight of said polymer matrix.

3. The biocompatible material according to claim 1, wherein said hyaluronic acid derivative is benzyl ester of hyaluronic acid having a degree of esterification of from 75 to 100%.

4. A process for the preparation of the biocompatible material according to claim 1, said process comprising the following steps:
   i) preparing a solution of poly-εCaprolactone in a suitable solvent or solvents mixture;
   ii) mixing the hyaluronic acid derivative in powder form with a pore-forming agent in an anhydrous environment;
   iii) pouring the solution of poly-εCaprolactone coming from step i) onto the mixture coming from step ii) and mixing together, thus obtaining the desired polymer matrix.

5. The process according to claim 4, wherein said solution in step i) is a solution of poly-εCaprolactone in a solvents mixture consisting of tetrahydrofurane, dimethylsulphoxide and ethanol.

6. The process according to claim 5, wherein said solvents mixture consists of 70.5% v/v tetrahydrofurane, 19.75% v/v dimethylsulphoxide and 9.75% v/v ethanol.

7. The process according to claim 4, wherein step i) is carried out at an initial temperature ranging from 30 to 40° C.

8. The process according to claim 4, wherein said pore-forming agent is a mixture of citric acid, NaCl and $NaHCO_3$.

9. The process according to claim 8, wherein said mixture consists of 93.8% w/w of NaCl having granulometry ranging from 315 to 400 μm, 3.5% w/w of $NaHCO_3$ having granulometry ranging from 140 to 400 μm and 2.7% of citric acid having granulometry lower than 200 μm.

10. The process according to claim 4, wherein the weight ratio of the hyaluronic acid derivative and PCL to the pore-forming agent is 1/10.

11. A prosthetic device comprising a reinforcing material in the form of fibres and/or tissues, and a lyophilisate of the biocompatible material according to claim 1, optionally coated by hyaluronic acid or a derivative thereof.

12. The prosthetic device according to claim 11, wherein said reinforcing material consists of fibres, uniformly distributed and/or arranged circumferentially in said lyophilisate of the biocompatible material.

13. The prosthetic device according to claim 11, wherein said reinforcing material consists of a tissue, placed parallel to the tibial plate and integrated in said lyophilisate of the biocompatible material.

14. The prosthetic device according to claim 11, wherein said reinforcing material consists of two tissues placed on a parallel plane to the tibial plate and integrated in said lyophilisate of the biocompatible material, one of said two tissues being limited to the peripheral portion only.

15. The prosthetic device according to claim 11, wherein said reinforcing material consists of one tissue placed on the edge of the meniscus and one placed on a plane parallel to the tibial plate, both tissues being integrated in said lyophilisate of the biocompatible material.

16. The prosthetic device according to claim 11, wherein said reinforcing material consists of one tissue on the edge of the meniscus connected with a second tissue placed on a parallel plane to the tibial plate, both tissues being integrated in said lyophilisate of the biocompatible material.

17. The prosthetic device according to claim 11, wherein said reinforcing material consists of a bioresorbable polymer and/or a non-bioresorbable polymer.

18. The prosthetic device according to claim 17, wherein said bioresorbable polymer is selected from the group consisting of polylactic acid, polyglycolic acid, collagen and mixtures thereof, and said non-bioresorbable polymer is selected from the group consisting of polypropylene, polyester, polyethylene terephthalate, polytetrafluoroethylene and mixtures thereof.

19. The prosthetic device according to claim 11, wherein said reinforcing material consists of fibres of polylactic acid.

20. The prosthetic device according to claim 11, wherein said reinforcing material consists of tissues of polylactic acid and polyglycolic acid.

21. The prosthetic device according to claim 11, further comprising partially differentiated and/or differentiated mesenchymal cells.

22. The prosthetic device according to claim 11, further comprising hyaline cartilage cells and/or meniscal fibrocartilage cells previously grown in vitro.

23. The prosthetic device according to claim 11, further comprising bone marrow taken and seeded during surgical implant.

24. The prosthetic device according to claim 11, having the shape of the meniscus or a portion thereof.

25. A prosthetic device according to claim 11, for the partial or total replacement of the meniscus, for the repair of damaged menisci, and for the regeneration of the meniscal fibrocartilage.

26. A process for the preparation of the prosthetic device according to claim 11, said process comprising the following steps:
 i') pouring the biocompatible polymer mixture of PCL and hyaluronic acid derivatives into a meniscus-shaped mould;
 ii') inserting a reinforcing material in the form of fibres and/or tissues into the polymer mixture;
 iii') drying the material coming from step ii') at room temperature, then removing the solidified material from the mould, dipping it into water and carry out one or more washings;
 iv') dipping the desiccated and washed material coming from step iii') into water at a temperature of 40° C.;
 v') removing water from the material coming from step iv') by lyophilisation by freeze drying technique;
 vi') sterilising the freeze-dried material coming from step iv').

27. The process according to claim 26, wherein the material coming from freeze-drying in step v') is immersed into an aqueous solution of hyaluronic acid or a derivative thereof, and subjected to one or more cycles of depressurisation and release to room pressure; then water is removed by a second lyophilisation step by freeze drying technique, and the freeze-dried material is finally sterilised as in step vi').

* * * * *